United States Patent [19]

McRae

[11] Patent Number: Plant 6,658

[45] Date of Patent: Mar. 7, 1989

[54] HYBRID ASIATIC LILY NAMED PROGRESS

[75] Inventor: Edward A. McRae, Boring, Oreg.

[73] Assignee: Melridge, Inc., Aurora, Oreg.

[21] Appl. No.: 80,496

[22] Filed: Jul. 31, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new hybrid lily variety distinguished by its large, deep orange, unspotted flowers having "clean" anthers which shed little pollen, the flowers being borne on a single tall stem from a raceme having five to eight buds, the blooms being of excellent form with long persistence both on the plant and as cut flowers. The plant itself is highly resistant to disease, shows high tolerance of virus, is an excellent garden plant, and its bulbs may be precooled and forced for cut flower production.

1 Drawing Sheet

BACKGROUND OF THE NEW PLANT

This new variety of lily plant originated as a seedling selected from a group of seedlings planted by me at Sandy, Oreg., and derived from the seeds of a hybrid developed by me with the object of producing lilies with a range of orange color tones which would produce little or no pollen and be well suited to forcing for cut flower production out-of-season. The parent hybrid resulted from my crossing the clonal cultivar 'Keystone', unpatented, with the clonal cultivar 'Sunkissed', unpatented, as the pollen parent. This particular seedling was selected for propagation and test because of the large size and upright orientation of its blooms and its vivid orange coloring with practically no spotting and with small anthers which shed very little pollen, features that are unique in this type of lily, and it was propagated by me and under my direction by bulb scale propagation at Sandy, Oreg., with results that appeared so satisfactory that propagation was continued through several successive generations by bulb scale propatation, as well as by natural propagation from bulblets, which demonstrated that the novel and distinctive characteristics of this new lily variety were fixed and hold true, under asexual propagation, from generation to generation.

Work with this new plant shows that the clone possesses to a high degree the desirable characteristics of hybrid vigor, great hardiness and disease resistance, as well as excellence of flower form, color and habit. Also, it has shown to be well suited to forcing out-of-season when the bulbs are dug at the appropriate time and properly precooled. For example, October-dug bulbs, properly precooled and potted in January, will flower under glass in western Oregon in an average of seventy to eight-five days with no supplemental lighting and at moderate greenhouse temperatures.

DESCRIPTION OF THE DRAWING

This new variety of lily plant is illustrated in the accompanying photographic drawing which, in full color, shows the open bloom and illustrates the flower form and tepal arrangement and shows in particular the novel and distinctive deep orange coloration of the flowers with their lack of spotting.

DESCRIPTION OF THE NEW VARIETY

The following is a detailed description of my new variety of Asiatic hybrid lily with nomenclature according to The International Lily Register, Second Edition, 1969, of The Royal Horticultural Society of London, England, the color designations being according to The R.H.S. Colour Chart published by the Society in 1966.

THE PLANT

Origin: Seedling.

Parentage:

*Seed parent.*—Lilium 'Keystone' (unpatented).

*Pollen parent.*—Lilium 'Sunkissed' (unpatented).

Classification:

*Horticultural.*—Division IA, Upright Asiatic Hybrid Lily, according to The Horticultural Classification of Lilies by The Royal Horticultural Society of London, England.

*Commercial.*—Hybrid Lilium Clone.

Form: Single stem, erect and stately.

Height: About 55 to 80 cm., from bulbs 15 to 18 cm. in circumference, provided that light levels are adequate. Low light levels may cause "stretching".

Growth: Vigorous and upright.

Foliage:

*Quantity.*—Abundant.

*Leaf size.*—About 8 to 10 cm. long and about 7 to 15 mm. wide.

*Leaf shape.*—Lanceolate with acuminate tip.

*Texture.*—Leathery.

*Aspect.*—Glossy and glaborous.

*Color.*—Deep green, somewhat lighter on the under side.

Bulbs:

*Size.*—Various, ranging up to 25 cm. in circumference in commercial use.

*Color.*—White.

THE BUD

Form: Substantially linear with obtuse tip.

Size: About 8 to 9 cm. long and about 7 cm. in circumference just prior to opening.

Opening rate: The bud opens slowly, taking about one hour in response to morning light.

Color: Soft Orange, 30C-D, underlying soft green just prior to opening and as the tepals unfurl.

Peduncle:

*Length.*—Averages 4 to 6 cm. but may elongate if light levels are too low or if the bulbs have been improperly stored prior to forcing.

*Color.*—Dark green, with deep plum overlay.

THE FLOWER

Blooming habit: Once annually and profusely in midseason.

Size: Large, averaging about 14 to 18 cm. in diameter.

Borne: As a single raceme having about five to eight buds from a bulb of about 18 cm. in circumference.

Shape: Cup-shaped upon first opening and flattening as the tepals recurve by the second day.

Tepalage:

*Number.*—Six.

*Arrangement.*—Hexagonal with inner petals in imbricate relation with the outer petals.

*Shape.*—Ovate with entire margins and acuminate tip.

*Size.*—Outer tepals average about 25 to 30 mm. wide. Inner tepals average about 40 to 45 mm. wide.

*Appearance.*—Shiny.

*Color.*—The base color is Orange-Red, 30A-B to 32B, the coloration being most intense just above the nectaries at the center of each tepal and at the apex of each tepal. The coloration is lighter parallel with the nectaries and over the body of each tepal. The nectaries are a softer orange color and are overlaid with short, white pubescence.

Tepal spotting: The tepals are usually unspotted, but occasionally a few tiny magenta spots may appear parallel with the brushmarks of color adjacent the nectaries.

Color changes: The flowers may become slightly redder-orange as they age but there is usually little color change if the light levels are adequate for cut flower maintenance. Under conditions of low light levels, the orange color may become lighter.

*Persistence.*—The tepals stay on the stem about three weeks.

Fragrance: None.

Disease resistance: The flower and plant are resistant to disease; in particular, they are resistant to Fusarium Bulb Rot and Botrytis Blight, as observed in western Oregon.

Lasting quality: The flower is long lasting, both on the plant and as a cut flower.

THE REPRODUCTIVE ORGANS

Stamens:

*Number.*—Six.

*Arrangement.*—Typical of genus Lilium.

*Anthers (dehisced).*—The Anthers are unusually small, averaging about 4 to 5 mm. long.

*Pollen.*—The anthers do not open fully and the small quantity of pollen that is exposed is Greyed Orange, 170A, to Orange-Red, 32A.

Pistil:

*Number.*—One.

*Style.*—Length: About 5 cm.

*Stigma.*—Medium in size and deep plum, Greyed Purple, 184B, in color.

Character of ovary: The ovary is characteristic of the genus Lilium.

THE FRUIT

Fertility: The fruit is fertile.

Shape: Ovoid.

Color at maturity: Soft brown, sometimes overlaid with soft plum.

This new lily variety most closely resembles the variety 'Halloween' (unpatented) but has flowers with "clean" anthers which shed very little pollen. The new plant also has deeper green leaves which are longer than those of 'Halloween'.

I claim:

1. The new and distinctive variety of Asiatic hybrid lily plant and parts thereof, substantially as herein shown and described, characterized by the rich orange coloration of its substantially unspotted flowers having small anthers which shed very little pollen; by the excellence of its flower form, its vigorous growth and rapid natural propagation, and its versatility both as a garden plant and as a cut flower producer.

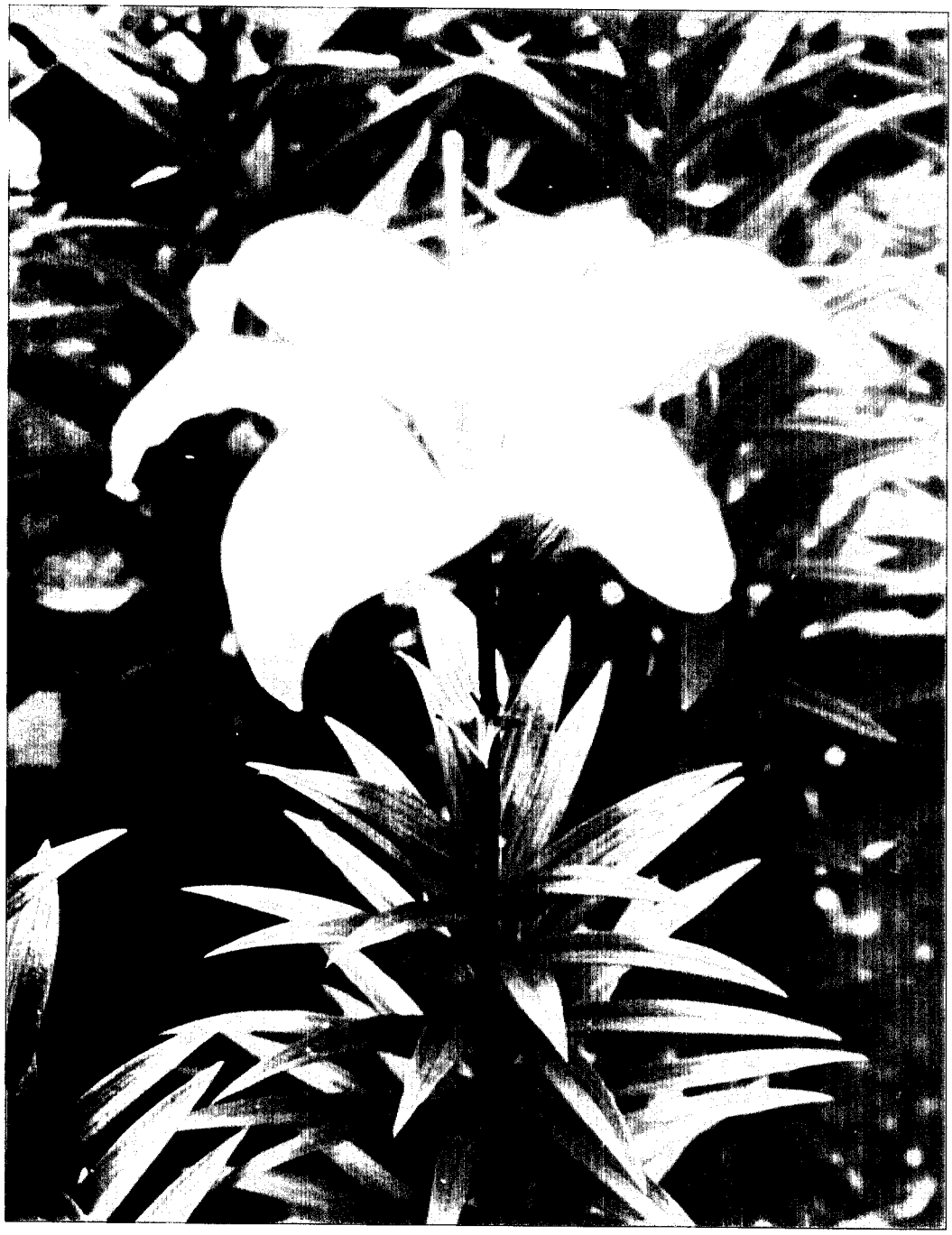

* * * * *